(12) United States Patent
Denick, Jr. et al.

(10) Patent No.: US 6,348,508 B1
(45) Date of Patent: Feb. 19, 2002

(54) METHOD FOR TREATING DRY EYE

(75) Inventors: John Denick, Jr., Pittsford; David J. Heiler, Avon; Zhenze Hu, Pittsford, all of NY (US); Joseph C. Salamone, Boca Raton, FL (US); Richard V. Smerbeck, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/542,332

(22) Filed: Apr. 4, 2000

(51) Int. Cl.[7] ........................ A61K 47/32; A61K 31/74; A61F 2/00; A61F 13/00
(52) U.S. Cl. .................... 514/772.4; 424/427; 424/434; 424/435; 424/78.04
(58) Field of Search ................. 424/427, 180, 424/78.04, 434, 435; 514/23, 772.4

(56) References Cited

U.S. PATENT DOCUMENTS

| | | | |
|---|---|---|---|
| 4,409,205 A | 10/1983 | Shively et al. ................ 424/78 |
| 4,436,730 A | 3/1984 | Ellis et al. .................. 424/180 |
| 5,209,927 A | 5/1993 | Gressel et al. ........... 424/78.04 |
| 5,294,607 A | 3/1994 | Glonek et al. ................ 514/76 |
| 5,358,706 A | 10/1994 | Marlin et al. ............ 424/78.04 |
| 5,401,327 A | 3/1995 | Ellis et al. .................... 134/42 |
| 5,422,116 A | * 6/1995 | Yen et al. .................... 424/427 |
| 5,645,827 A | 7/1997 | Marlin et al. ............ 424/78.04 |
| 6,037,328 A | * 3/2000 | Hu et al. ...................... 514/23 |

FOREIGN PATENT DOCUMENTS

| | | | |
|---|---|---|---|
| DE | 3440352 | 5/1986 | |
| EP | 088770 A1 | 1/1999 | ............ A61K/9/00 |

OTHER PUBLICATIONS

"Mucus Secretory Vesicles in Conjunctival Epithelial Cells of Wearers of Contact Lenses", Archives of Ophthalmology, vol. 98, pp. 1843–1846 (1980).

* cited by examiner

*Primary Examiner*—Thurman K. Page
*Assistant Examiner*—Blessing Fubara
(74) *Attorney, Agent, or Firm*—Robert B. Furr, Jr.

(57) ABSTRACT

The present invention is directed to a method of treating dry eye by instilling eyedrops of a composition containing a cationic cellulosic polymer. Such compositions have been found to alleviate the symptoms of dry eye without requiring the presence of anionic therapeutic agents. Low ionic strength solutions are particularly preferred.

36 Claims, 4 Drawing Sheets

METHOD FOR TREATING DRY EYE

FIELD OF THE INVENTION

This invention relates to a method for treating dry eye. In particular, solutions comprising a cationic cellulosic polymer have been found useful for alleviating the symptoms of dry eye.

BACKGROUND

Dry eye, also known generically as keratoconjunctivitis sicca and dyslacrima, is a common ophthalmological disorder affecting millions of people. A patient with dry eye may experience burning, a feeling of dryness and persistent irritation. In severe cases, dry eye can seriously impair a person's vision and hence handicap the sufferer in activities such as driving. Certain diseases such as Sjogren's disease manifest dry eye symptoms. Also, as people age, the lacrimal ducts in the eye may produce less moisture, resulting in eyes that become dry, inflamed, itchy and gritty.

Although it appears that dry eye may result from a variety of underlying, unrelated pathogenic causes, all presentations of the condition share a common effect, namely the breakdown of the pre-ocular tear film, which commonly results in dehydration of the exposed outer surface and hence the symptoms described above.

A number of approaches exist for the treatment of dry eye. One common approach has been to supplement the ocular tear film using artificial tears instilled throughout the day. Examples of the tear substitute approach include the use of buffered, isotonic saline solutions and aqueous solutions containing water-soluble polymers that render the solutions more viscous and thus less easily shed by the eye by the washing action of the tear fluid. See, for example, U.S. Pat. No. 5,209,927 to Gressel, et al.; U.S. Pat. No. 5,294,607 to Glonek, et al.; and U.S. Pat. No. 4,409,205 to Shively.

Although these approaches have met with some success in some cases, significant challenges in the treatment of dry eye nevertheless remain. Problems include the fact that the use of tear substitutes, while temporarily effective, generally require repeated application over the course of a patient's waking hours, not uncommonly ten to twenty times over the course of a day. Such an approach is not only inconvenient and time consuming, but not very effective in preventing at least the initiation of dry-eye symptoms. Although increasing the viscosity of the dry-eye product may extend the product's duration in the eye to a limited extent, still further increases in duration would be highly desirable.

U.S. Pat. No. 5,645,827 to Marlin, et al. discloses the use of compositions comprising a cationic polysaccharide in combination with an anionic therapeutic agent, for example, hyaluronic acid or its salt, which is a known demulcent for the treatment of dry eye. Marlin, et al. believe that the anionic therapeutic agent is electrostatically bonded to the cationic polysaccharide which in turn is substantive to the mucosal surface. Substantivity is characterized by an increase of the cationic polysaccharide on the mucosal surface and can be measured through the use of an ocular fluorometer. European Application 088770 Al to Marlin et al. discloses cationic cellulose polymers to deliver cationic therapeutic agents, especially for the treatment of glaucoma.

U.S. Pat. Nos. 4,436,730 and 5,401,327 to Ellis, et al. disclose the use of cationic cellulosic derivatives in contact-lens treating solutions, including the combination of a cationic cellulose polymer and an ethoxylated glucose such as glucam. In column 4, lines 42–57, the latter patent states that the combination of a cationic cellulose material with a PEO component such as glucam is particularly advantageous for the reason that the cationic component complexes with the PEO component and the complex more strongly absorbs on the lens surface. The cationic cellulose polymer and entangled PEO is believed to reach into the aqueous phase to provide cushioning and protein resistance.

German Application DE 3440352 teaches a treatment for dry eye that contains an acrylate-based dry eye gel, containing from 0.2 to 1.0 parts acrylate polymer such as Carbopol), 0.15 to 3 parts base (such as NaOH), and remainder water; and a dry eye solution containing 0.1 to 1 part by weight water-soluble cationic cellulose derivatives (such as various UCAREO® Polymer JR), 0.5 parts by weight of an isotonic agent and remainder water.

In view of the above, it would be desirable to provide an eye-drop solution that will better alleviate the symptoms of dry eye and that is safe, convenient and economical to use. In particular, it would be highly desirable to develop a product having significantly greater duration of efficacy, in order to significantly decrease the number of times that the product may need to be administered to the eye, over the course of a day, in order to effectively treat the symptoms of dry eye.

SUMMARY OF THE INVENTION

The present invention is directed to a method of treating dry eye employing a solution comprising an effective amount of a cationic cellulose for alleviating the symptoms of dry eye. Such solutions are effective in the absence of hyaluronic acid and other anionic therapeutic agents. The invention is also directed to a method of using the foregoing composition to treat the symptoms of dry eye. In one preferred embodiment, the method employs a solution having low ionic strength. In another preferred embodiment, the method employs a solution having relatively low concentrations of mono- or di-saccharides. In a particularly preferred embodiment, the solution of the invention is essentially free of chloride ions and essentially free of mono- or di-saccharides.

BRIEF DESCRIPTION OF THE DRAWINGS

The objects, features and advantages of the various embodiments of the present invention will become more readily apparent from the following detailed description together with the following drawings.

DETAILED DESCRIPTION OF THE INVENTION

The present invention is directed to a method of treating the symptoms of dry eye employing an ophthalmic solution that can be applied in the form of drops and which comprises a cationic cellulosic polymer that exhibits prolonged duration in the eye. A wide variety of cationic cellulosic materials may be used in the practice of this invention. Specific examples include cellulosic polymers containing N,N-dimethylaminoethyl groups (either protonated or quaternized) and cellulosic polymers containing N,N-dimethylamino-2-hydroxylpropyl groups (either protonated or quaternized). Cationic cellulosic polymers are commercially available or can be prepared by methods known in the art. As an example, quaternary nitrogen-containing ethoxylated glucosides can be prepared by reacting hydroxyethyl cellulose with a trimethylammonium-substituted epoxide. Various preferred cationic cellulosic polymers are commercially available, for example water-soluble polymers available under the CTFA (Cosmetic, Toiletry, and Fragrance Association) designation Polyquaternium-10. Such polymers are commercially available under the tradename UCARE® Polymer from Amerchol Corp., Edison, N.J., USA. These polymers contain quaternized N,N-dimethylamino groups along the cellulosic polymer chain.

The cationic cellulosic component may be employed in the compositions at about 0.01 to about ten (10) weight percent of the composition, preferably at about 0.05 to about five (5) weight percent, with about 0.1 to about one (1) weight percent being especially preferred. Suitable cationic cellulosic materials have the following formula:

Wherein $R_1$ $R_2$ and $R_3$ are selected from H, derivatives of $C_1$-$C_2$, carboxylic acid, $C_1$-$C_{20}$ alkyl groups, $C_1$ to $C_3$ monohydric and dihydric alkanols, hydroxyethyl groups, hydroxypropyl groups, ethylene oxide groups, propylene oxide groups, phenyl groups, "Z" groups and combinations thereof. At least one of $R_1$, $R_2$, and $R_3$ is a Z group.

The nature of the "Z" groups is:

where:

R', R" and R'" can be H, $CH_3$, $C_2H_5$, $CH_2CH_2OH$ and x=0–5, y=0–4, and z=0–5

$X^{31}$ =Cl$^-$, Bra$^-$, I$^-$, $HSO_4^-$, $CH_3SO_4^-$, $^H{_2}PO_4^-$, $NO_3^-$

Optionally, one or more additional polymeric or non-polymeric demulcents may be combined with the above-named ingredients. Demulcents are known to provide wetting, moisturizing and/or lubricating effects, resulting in increased comfort. Polymeric demulcents can also act as a water-soluble viscosity builder. Included among the water-soluble viscosity builders are the non-ionic cellulosic polymers like methyl cellulose, hydroxyethyl cellulose, hydroxypropyl cellulose, and carboxymethyl cellulose, poly(N-vinylpyrrolidone), poly(vinylalcohol) and the like. Such viscosity builders or demulcents may be employed in a total amount ranging from about 0.01 to about 5.0 weight percent or less. Suitably, the viscosity of the final formulation is 10 cps to 50 cps. Comfort agents such as glycerin or propylene glycol can also be added.

In contrast to the prior art, the solutions of the present invention are effective in the absence of conventional anionic therapeutic agents for the treatment of dry eye. Prior art anionic therapeutic agents include glycosaminoglycans such as hyaluronic acid, hylan, hylaluronan, heparin, heparan sulfate, chondroitin sulfate, keratin sulfate and dermatan sulfate. Various glycosaminoglycans absent from the present composition are listed in U.S. Pat. No. 5,358,706, hereby incorporated by reference. Hyaluronic acid is an anionic biopolymer that has been identified as useful in the treatment of the symptoms of dry eye. Synthetic anionic polymers for the treatment of dry eye also include carboxy-vinyl polymers known as Carbopol,® commercially available from B.F. Goodrich, as described in U.S. Pat. No. 5,209,927 to Gressel, et al.

Thus, it has been found that the cationic polysaccharides are, in themselves, effective for the treatment of dry eye. Without wishing to be bound by theory, it may be that the polymers, after binding to the mucosal tissue of the eye, in turn promote the mucin in the eye, either by supplementing the mucin and/or by helping to bind and maintain mucin on the surface of the eye. Mucins are proteins, which are heavily glycosylated with glucosamine-based moieties. Mucins have been shown to be secreted by vesicles and discharged on the surface of the conjunctival epithelium of the eye. See for example, Greiner, et al., "Mucus Secretory Vesicles in Conjunctival Epithelial Cells of Wearers of Contact Lenses," *Archives of Ophthalmology*, Vol. 98, pages 1843–1846 (1980). Mucins provide lubrication and additionally attract and hold moisture and sebaceous material for lubrication.

The present composition may also contain a disinfecting amount of a preservative or an antimicrobial agent. A particularly preferred preservative is sorbic acid (0.15%). Antimicrobial agents are defined as organic chemicals that derive their antimicrobial activity through a chemical or physiochemical interaction with the microbial organisms. For example, biguanides include the free bases or salts of alexidine, chlorhexidine, hexamethylene biguanides and their polymers, and combinations of the foregoing. The salts of alexidine and chlorbexidine can be either organic or inorganic and are typically gluconates, nitrates, acetates, phosphates, sulfates, halides and the like. The preferred biguanide is the hexamethylene biguanide commercially available from Zeneca, Wilmington, DE under the trademark Cosmocil™ CQ. Generally, the hexamethylene biguanide polymers, also referred to as polyaminopropyl biguanide (PAPB), have molecular weights of up to about 100,000.

If used in the subject solution, the antimicrobial agent should be used in an amount which will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test-July, 1985 Contact Lens Solution Draft Guidelines). Typically, such agents are present in concentrations ranging from about 0.00001 to about 0.5% (w/v), and more preferably, from about 0.00003 to about 0.05% (W/V).

The aqueous solutions employed in this invention may contain, in addition to the active ingredients described above, one or more other components that are commonly present in ophthalmic solutions, for example, buffers, stabilizers, tonicity agents and the like, which aid in making ophthalmic compositions more comfortable to the user. The aqueous solutions of the present invention are typically adjusted with tonicity agents to approximate the tonicity of normal lacrimal fluids which is equivalent to a 0.9% solution of sodium chloride or 2.8% of glycerol solution. The solutions are made substantially isotonic with physiological saline used alone or in combination; otherwise, if simply blended with sterile water and made hypotonic or made hypertonic, the lenses will lose their desirable optical parameters. Correspondingly, excess salt or other tonicity agents may result in the formation of a hypertonic solution that will cause stinging and eye irritation. An osmolality of about 225 to 400 mOsm/kg is preferred, more preferably 280 to 320 mOsm/kg.

In a preferred embodiment, the ionic strength of the present solutions is relatively low. In this preferred embodiment of the invention, low ionic strength has surprisingly been found to be associated with improved performance. The solutions preferably contain less than 4 mM calcium chloride, and is more preferably essentially free of calcium chloride. The solutions preferably contain less than 150 mM sodium chloride, more preferably less than 75 mM sodium chloride. The solutions preferably contain less than 15 mM potassium chloride, more preferably less than 6 mM potassium chloride. In one preferred embodiment, the chloride ion concentration of the solution is less than 300 mM, more preferably less than 100 mM.

The solutions of the present invention preferably contain less than 300 mOsm/kg equivalents of a mono- or di-saccharide, more preferably less than 100 mOsm/kg of a mono- or a di-saccharide, and most preferably contain essentially no mono- or di-saccharide. Maintaining the concentrations of mono- and di-saccharide below the specified limits has surprisingly been found to be associated with improved performance.

In an alternate embodiment, the solutions of the present invention may contain one or more ionic or non-ionic surfactants and may be used as cleaning and/or conditioning solutions for hydrogel or RGP (rigid-gas-permeable) contact lenses. Effective amounts of surfactant are preferably in the range of from about 0.01% to about 5% by weight. In a preferred embodiment of the surfactant-containing solutions of the invention, the surfactant is a neutral or non-ionic surfactant.

The pH of the present solutions used to treat dry eye should be maintained within the range of 5.0 to 8.0, more preferably about 6.0 to 8.0, most preferably about 6.5 to 7.8; suitable buffers may be added, such as borate, citrate, bicarbonate, TRIS and various mixed phosphate buffers (including combinations of $Na_2HPO_4$, $NaH_2PO_4$ and $KH_2PO_4$) and mixtures thereof. Borate buffers are preferred, particularly for enhancing the efficacy of PAPB. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions, which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

The solutions employed in the present invention can be prepared by a variety of techniques. One method employs two-phase compounding procedures. In the first phase, about 30 percent of the distilled water is used to dissolve the cationic cellulosic polymer by mixing for about 30 minutes at around 50° C. The first-phase solution is then autoclaved at about 120° C. for 30 minutes. In a second phase, alkali metal chlorides, sequestering agents, preservatives and buffering agents are then dissolved in about 60 percent of the distilled water under agitation, followed by the balance of distilled water. The second-phase solution can then be sterilely added into the first-phase solution by forcing it through an 0.22 micron filter by means of pressure, followed by packaging in sterilized plastic containers.

As indicated above, the present invention is useful for treating dry eye, or, more specifically, its symptoms. For that purpose, compositions for use in the present invention may be sold in a wide range of small-volume containers from 1 to 30 ml in size. Such containers can be made from HDPE (high density polyethylene), LDPE (low density polyethylene), polypropylene, poly(ethylene terepthalate) and the like. Flexible bottles having conventional eye-drop dispensing tops are especially suitable for use with the present invention.

The above-described solutions, in accordance with the present invention, may be used by instilling, for example, about one (1) or three (3) drops in the affected eye(s) as needed, for the temporary relief of burning and irritation due to dryness in the eye and for use as a protectant against further irritation, or to relieve dryness to the eye.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

EXAMPLE 1

An aqueous solution for use in treating the symptoms of dry eye according to the present invention, by means of eyedrops of the solution administered to the eye, is prepared with the following ingredients in water:

TABLE 1

| Ingredient | mg/g | % w/w |
| --- | --- | --- |
| UCARE ® Polymer JR 30 m | 5.00 | 0.50 |
| Benzalkonium Chloride, 50% | 0.22 | 0.022 |
| Boric Acid | 10.00 | 1.00 |
| Sodium Borate | 1.10 | 0.11 |
| Glycerin | 10.00 | 1.00 |

The formulation is prepared in bulk as follows. In a 316-grade stainless-steel-jacketed pressure kettle equipped with agitation, distilled water is added in the amount of about 800 g and heated to 60° to 70° C., preferably 65° C. Under agitation the following batch quantities of the following ingredients are added, wherein after one ingredient is dissolved or hydrated, the next is added: Polymer JR, Boric Acid, Sodium Borate, Benzalkonium Chloride, Glycerin. Agitation is maintained throughout the entire processing of the batch. Upon dissolution of these components, the batch is charged with purified water to 98 percent of the final weight. The solution is mixed for a minimum of thirty(30) minutes to ensure complete dissolution. If necessary, the pH is adjusted to 6.5 to 7.4 at 25° C. with 2.5 N NaOH or 1N HC1 and measured at 6.8. The osmolality is measured at 300 mOsm/Kg. The solution may be sterilized by autoclave at 121–124° C. for thirty (30) to forty-five (45) minutes and then immediately cooled to 40° C., after which a sufficient quantity of cool purified water may be added to obtain the final weight. For best product clarity, the finished solution should be aseptically passed through a sterile 40–50 micrometer polishing filter. For use in the above process, suitable polishing filters include Pall Rigimesh™ RR 40 micrometer and Filterite Dynalloy™ 30 micrometer PSP 12-10SL-M7 filters.

EXAMPLE 2

This example illustrates the effective duration in the eye of solutions according to the present invention as measured using FITC-dextran (also referred to as "FD"). This material, having a molecular weight of 40,000, is commercially available from the Sigma Chemical Company (MO, USA). The control solution was five (5) percent FD dissolved in distilled, de-ionized water.

Test solution 1 contained five (5) percent FITC-dextran with the combination of UCARE® Polymer JR 30M (0.5 percent) and Carbowax® Sentry® Polyethylene Glycol 20M (0.5 percent). Test Solution 2 contained five (5) percent FITC-dextran with UCARE® Polymer JR 30M (0.5 percent) only. The two solutions were tested in triplicate in male New Zealand rabbits (weighing 1.5 to 2 kilograms). The test solution was administered into the right eye and the control solution was administered into the left eye of the rabbit. The solutions (25 mg) were instilled in the lower cul-de-sac of each rabbit eye. All solutions were administered with a micropipettor. The eyes were held closed for thirty (30) seconds after instillation.

Tear fluid was collected at 0.5, 1, 2, 3, 4.5 and 6 hours using 2 μl disposable glass capillaries. The upper eyelid of the rabbit eye was held up, and the capillary tube was placed in the upper cul-de-sac. The tear was collected by gently drawing the end of the tube between the globe of the eye and the eyelid for about one minute. During sampling, contact between the capillary tip and any visible gel lumps was avoided. The fluid in the capillaries was flushed into tubes containing one ml of water, and the resulting samples were stored at 4° C. until analysis of the FD content. The concentration of FD in the samples was determined using a spectrofluorophotometer. The excitation wavelength was 491 nm, and the emission wavelength was 513 nm. A standard curve was obtained using solutions containing 0.05, 0.1, 0.2, 0.4, 0.6 and 1.0 μg/ml of FD. Because the volume of tears in each rabbit eye is different, the concentration of FD in one ml of tear was calculated. The FD concentrations versus time curves were plotted.

A non-parametric statistical test (Wilcoxon rank sum test) was used to compare the FD concentrations in tears, obtained following administration of the test solution and the control.

Figure 1:
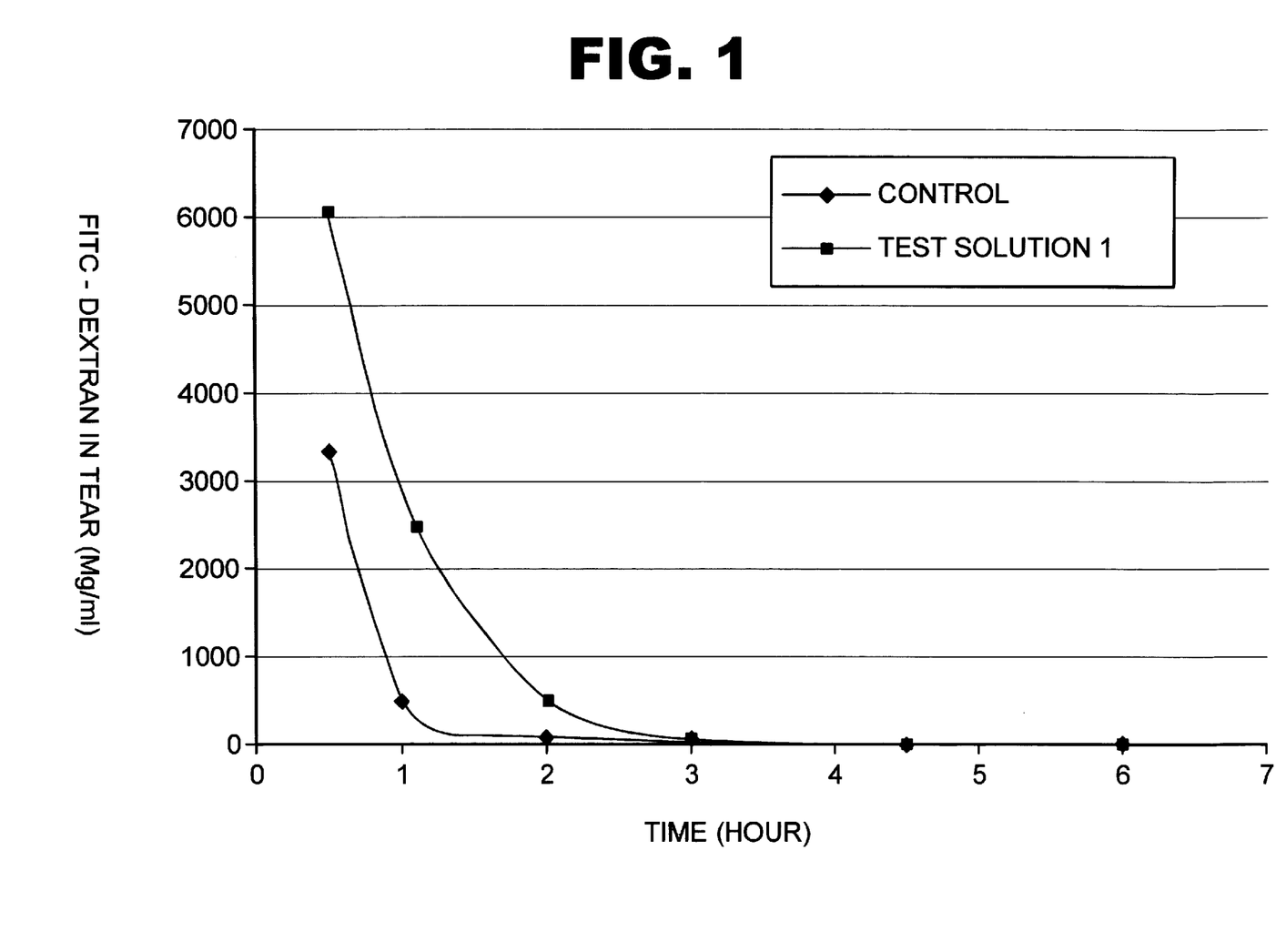
FIG. 1 shows the results from the tests of Example 2 below, involving the measurement of the concentration of FITC-Dextran in a solution according to the present invention versus the concentration of FITC-Dextran in a control solution over a period of six hours in rabbit eyes.
Figure 2:
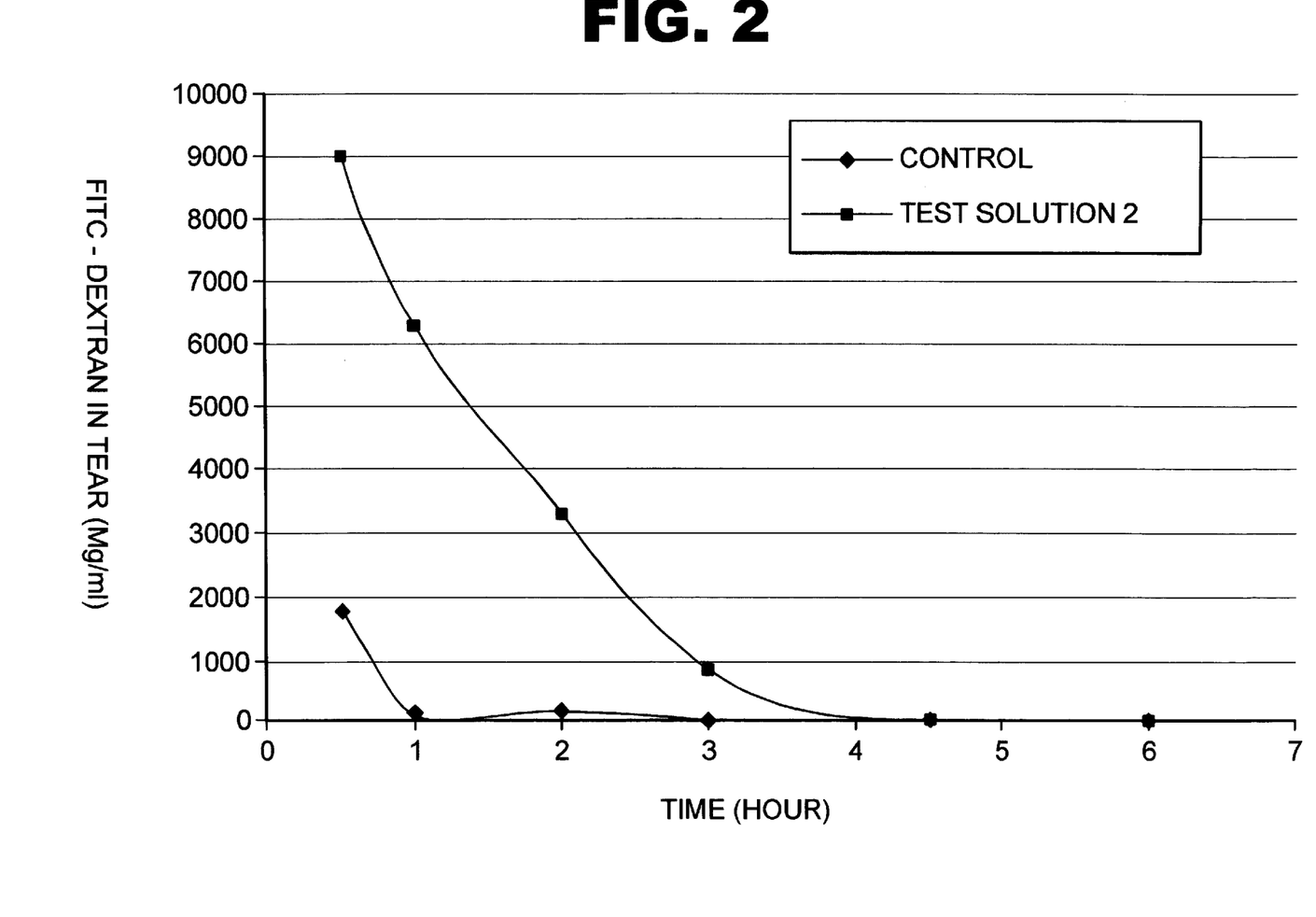
FIG. 2 shows the results from the tests of Example 2 below, involving measurement of the concentration of FITC-Dextran in a second solution according to the present invention versus the concentration of FITC-Dextran in a control solution over a period of six hours in rabbit eyes.

FD concentrations in the tear fluid obtained following administration of the test solution 2 were higher than those obtained using the control solution ($\alpha=0.05$), which was maintained for three (3) hours. For the test solution 1, the resulting FD concentrations, although not statistically significant due to the limited sample size, were also higher than those of the control solution up to two (2) hours. The results for the concentration of FITC-Dextran in tears (mg/ml) over time (n=3) are shown in Table 2 below for the average. Figures 1 and 2 show a comparison to the control for the test solutions 1 and 2, respectively, in tear over six (6) hours.

TABLE 2

| Test Solution | Time (Hour) | FITC-Dextran Concentration | | Wilcoxon Rank |
|---|---|---|---|---|
| | | Control | Test | Sum Test ($\alpha = 0.05$) |
| 1 | 0.5 | 3322 | 6089 | no difference |
| | 1 | 409 | 2426 | no difference |
| | 2 | 83 | 541 | no difference |
| | 3 | 17 | 28 | no difference |
| | 4.5 | 4 | 21 | no difference |
| | 6 | 48 | 4 | no difference |
| 2 | 0.5 | 1793 | 9000 | Test > Control |
| | 1 | 161 | 6272 | Test > Control |
| | 2 | 164 | 3431 | Test > Control |
| | 3 | 47 | 870 | Test > Control |
| | 4.5 | 20 | 12 | no difference |
| | 6 | 31 | 99 | no difference |

EXAMPLE 3

This example illustrates the effectiveness of the present invention to stabilize the tear fillm and decrease the symptoms of dry eye in an animal model. New Zealand white rabbits had the nictitating membrane and the accessory and main lacrimal glands surgically removed from their right eye. As a result, the tear film stability was significantly reduced compared to that of the left contralateral control eye. The non-invasive break up time (NIBUT) was then measured in minutes for each eye. After baseline measurements were taken in the right eye, one (1) drop of the test solution was administered and the NIBUT was measured immediately and at 5, 15 and 30 minutes after instillation. Five (5) solutions were tested. The first was a borate-buffered saline (BBS); the second was a composition containing 0.5% Polymer JR and 1% Glycerin in the BBS; and the third was a combination of 1% Propylene Glycol and 0.3% Glycerin in the BBS. The compositions of the fourth through eighth solutions are shown below in Table 3. The effectiveness of each solution is represented in terms of percent of increase in NIBUT over baseline is shown in Tables 4 through 7, below.

Figure 3:
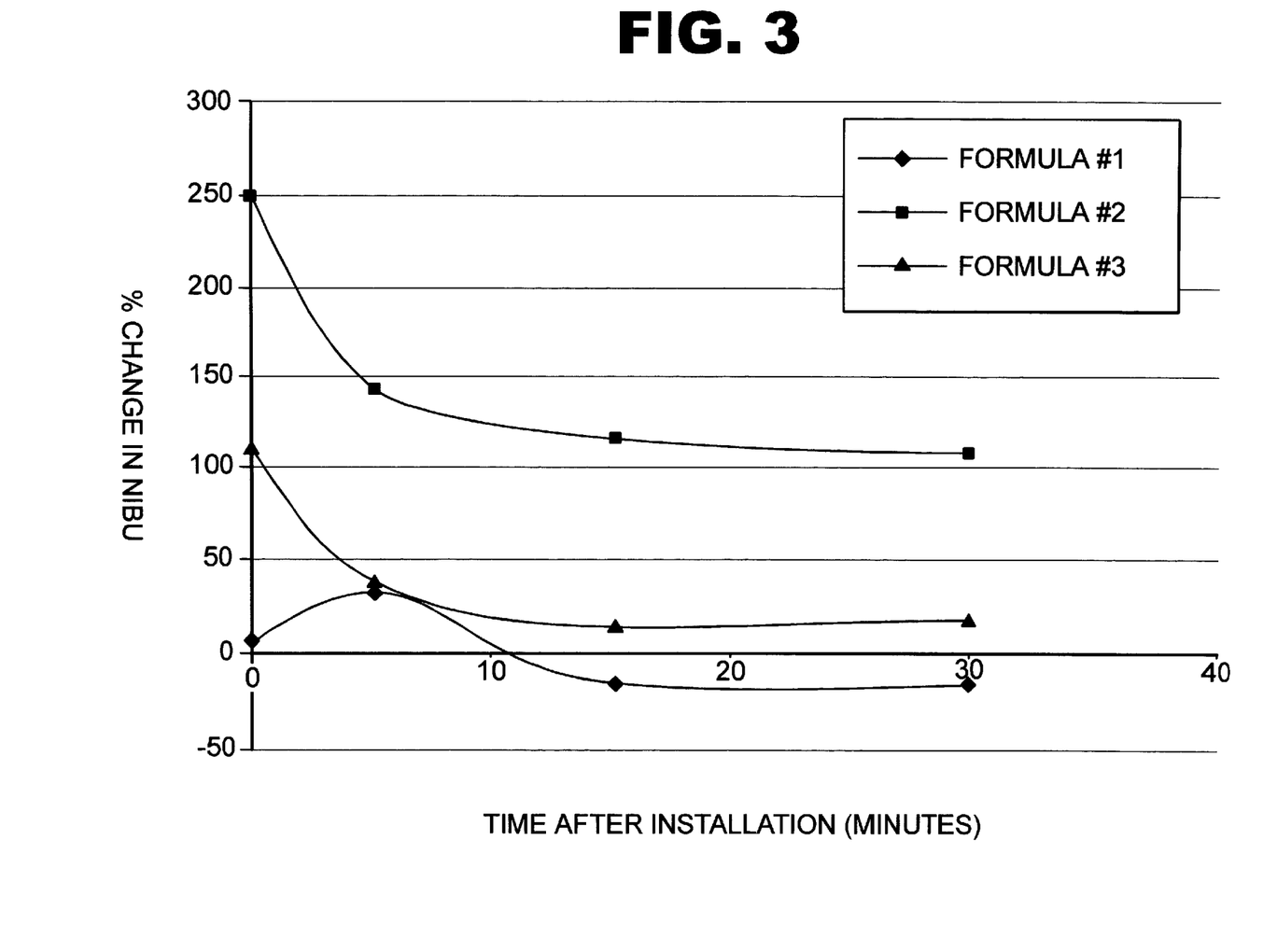
FIGS. 3 and 4 show the results for the tests of Example 3 below, involving measurement of the increase in non-invasive break up time (NIBUT) of tear film over a period of instillation of a solution according to present invention over thirty (30) minutes in rabbit eyes.
Figure 4:
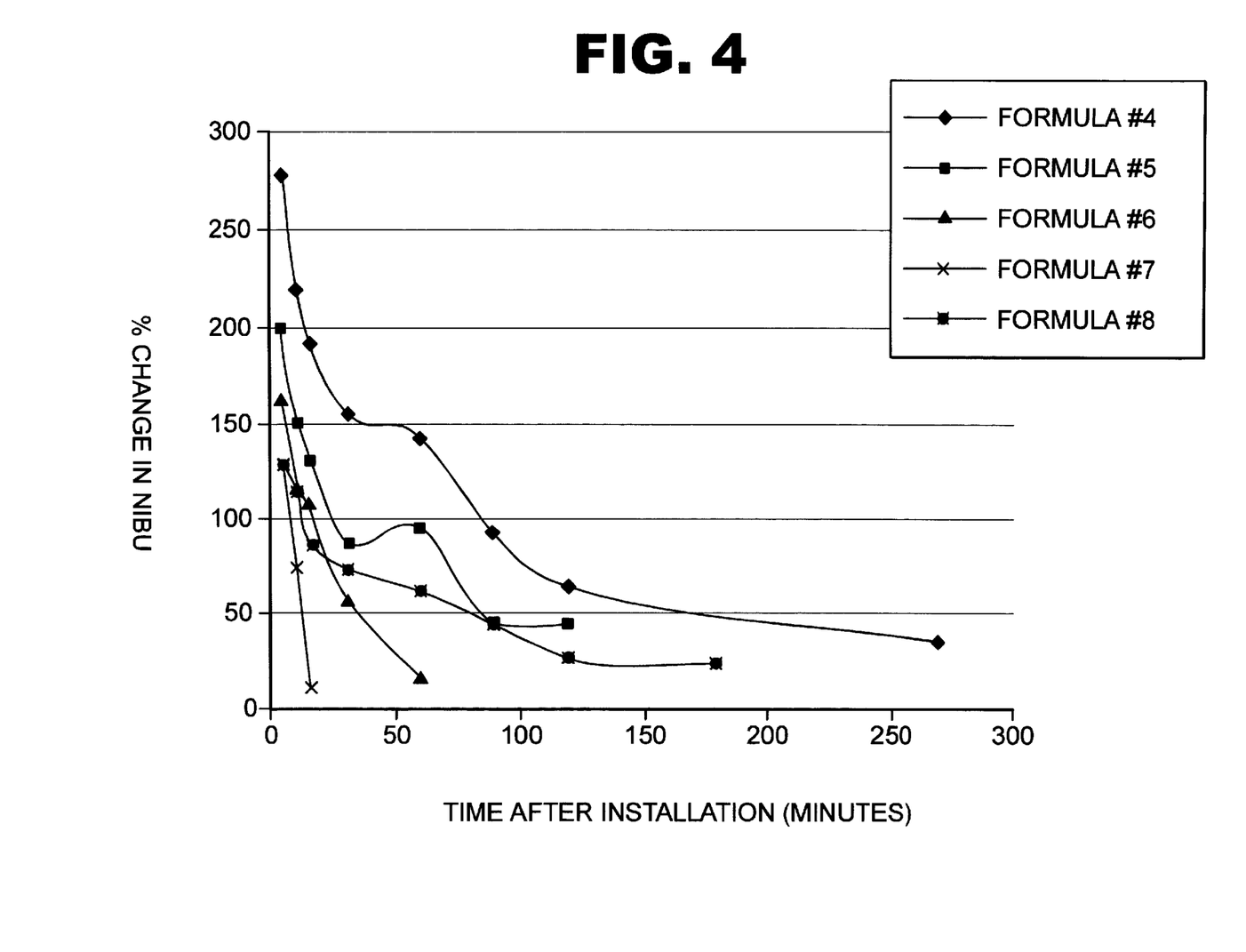

The results were also illustrated in FIGS. 3 and 4. Initially, both solutions 2 and 3 were very effective while solution 1 (saline control) had little effect. Solution 2's effect was significantly longer lasting than the solution 3's; in fact, at 30 minutes after instillation, the solution 2 still restored the tear film stability by 113.8% compared to 20.1% for the solution 3. Solution 4, which was free of added sodium chloride, potassium chloride and calcium chloride, restored tear fihn stability by 154% at 30 minutes after instillation.

TABLE 3

| Ingredients | Concentration % w/w | Solution 4 | Solution 5 | Solution 6 | Solution 7 | Solution 8 |
|---|---|---|---|---|---|---|
| Polymer JR | 0.2 | X | X | X | X | X |
| PVP | 1 | X | X |  | X | X |
| Glycerin | 1 | X | X | X | X |  |
| Propylene Glycol | 1 | X |  |  | X |  |
| Dextrose Monohydrate |  |  |  |  | 2.5% | 4.7% |
| Sodium Chloride | 0.267 |  | X |  |  |  |
| Potassium Chloride | 0.132 |  | X |  |  |  |
| Calcium Chloride dihydrate | 0.0294 (2 mM) |  | X | X |  | X |

Other common ingredients in Formulations A–E: 0.3% Boric Acid, 0.035% Sodium Borate and 0.9 ppm PHMB.

TABLE 4

| Test Solution | 0 Min | 5 Min | 15 Min | 30 Min |
|---|---|---|---|---|
| 1 (Control) | 7.9 | 31.8 | −13.4 | −14.1 |
| 2 | 248.7 | 149.7 | 120.6 | 113.8 |
| 3 | 115.7 | 39.1 | 15.9 | 20.1 |

TABLE 5

| Test Solution | 0 Min | 5 Min | 15 Min | 30 Min |
|---|---|---|---|---|
| 4 | 274.9 | 214.4 | 194 | 154 |
| 5 | 195.1 | 155.7 | 135.4 | 86 |

TABLE 6

| Time (min) | Solution #4 Mean | Solution #5 Mean | Solution #6 Mean | Solution #7 Mean | Solution #8 Mean |
|---|---|---|---|---|---|
| 5 | 274.9 | 195.1 | 163.2 | 129.5 | 125.9 |
| 10 | 214.4 | 155.7 | 123.5 | 73.4 | 119.1 |
| 15 | 194.0 | 135.4 | 112.2 | 12.5 | 88.0 |
| 30 | 154.0 | 86.0 | 58.1 |  | 73.5 |
| 60 | 142.2 | 94.1 | 15.9 |  | 60.3 |
| 90 | 91.1 | 43.7 |  |  |  |
| 120 | 63.2 | 43.1 |  |  | 27.1 |
| 180 |  |  |  |  | 23.3 |
| 270 | 36.7 |  |  |  |  |

TABLE 7

| Time (min.) | Mean |
|---|---|
| Solution #8 | |
| 5 | 125.9 |
| 10 | 119.1 |
| 15 | 88.0 |
| 30 | 73.5 |
| 60 | 60.3 |
| 120 | 27.1 |
| 180 | 23.3 |
| Solution #4 | |
| 5 | 274.9 |
| 10 | 214.4 |

TABLE 7-continued

| Time (min.) | Mean |
|---|---|
| 15 | 194.0 |
| 30 | 154.0 |
| 60 | 142.2 |
| 90 | 91.1 |
| 120 | 63.2 |
| 270 | 36.7 |

Many other modificaations and variations of the present invention are possible in light of the teachings herein. It is therefore understood that, within the scope of the claims, the present invention can be practiced other than as herein specifically described.

What is claimed is:

1. A method of treating dry eye comprising administering an aqueous solution comprising 0.001 to 10.0 percent by weight of a cationic cellulosic polymer, provided that the solution has a chloride ion concentration of no more than 300 mM and does not contain an anionic therapeutic agent for the treatment of dry eye.

2. The method of claim 1 wherein said aqueous solution further comprises providone.

3. The method of claim 1, further comprising at least one tonicity agent which is present in an amount of 0.01 to 10.0 percent by weight.

4. The method of claim 1, further comprising an effective amount of a buffering agent.

5. The method of claim 1, wherein the solution further comprises a sequestering agent which is present in an amount of 0.01 to 5.0% by weight.

6. The method of claim 1, fuirther comprising one or more non-ionic polymeric or non-polymeric demulcents.

7. A method of treating dry eye comprising instilling in the eye drops of a sterile aqueous solution consisting essentially of:
   (a) 0.05 to 5.0 percent by weight of a cationic cellulosic polymer;
   (b) at least one non-ionic tonicity agent which is present in an amount of 0.01 to 10.0 percent by weight;
   (c) an effective amount of a buffering agent to maintain the pH from 6 and 8;
   (d) a non-ionic polymeric or non-polymeric demulcent.

8. The method of claim 6, wherein the demulcent is selected from the group consisting of glycerin, propylene glycol and combinations thereof.

9. The method of claim 6, wherein the demulcent is selected from the group consisting of non-ionic cellulosic polymers, povidone, poly(vinyl alcohol) and combinations thereof.

10. The method of claim 9 wherein the demulcent is povidone.

11. A method of treating dry eye comprising administering an aqueous solution comprising 0.001 to 10.0 percent by weight of a cationic cellulosic polymer and an effective amount of a biguanide antimicrobial agent, provided that the solution does not contain an anionic therapeutic agent for the treatment of dry eye.

12. The method of claim 11 further comprising at least one tonicity agent which is present in an amount of 0.01 to 10.0 percent by weight.

13. The method of claim 11, further comprising an effective amount of a buffering agent.

14. The method of claim 11, wherein the solution further comprises a sequestering agent which is present in an amount of 0.01 to 5.0% by weight.

15. The method of claim 11 further comprising one or more non-ionic polymeric or non-polymeric demulcents.

16. A method of treating dry eye comprising instilling in the eye drops of a sterile aqueous solution consisting essentially of:
   (a) 0.001 to 5.0 percent by weight of a cationic cellulosic polymer;
   (b) at least one tonicity agent which is present in an amount of 0.01 to 10.0 percent by weight;
   (c) an effective amount of a buffering agent to maintain the pH from 6 and 8;
   (d) a non-ionic polymeric or non-polymeric demulcent and
   (e) an effective amount of a biguanide antimicrobial agent.

17. The method of claim 16, wherein the demulcent is selected from the group consisting of glycerin, propylene glycol and combinations thereof.

18. The method of claim 16 wherein the demulcent is selected from the group consisting of non-ionic cellulosic polymers, povidone, poly(vinyl alcohol) and combinations thereof.

19. The method of claim 1 wherein said aqueous solution contains less than 4 mM calcium chloride.

20. The method of claim 19 wherein said aqueous solution contains is essentially free of calcium chloride.

21. The method of claim 1 wherein said aqueous solution contains less than 150 mM sodium chloride.

22. The method of claim 21 wherein said aqueous solution contains less than 75 mM sodium chloride.

23. The method of claim 1 wherein said aqueous solution contains less than 15 mM potassium chloride.

24. The method of claim 23 wherein said aqueous solution contains less than 6 mM potassium chloride.

25. The method of claim 1 wherein said aqueous solution contains less than 300 mOsmol/kg equivalents of a mono- or di-saccharide.

26. The method of claim 25 wherein said aqueous solution contains less than 100 mOsmol/kg equivalents of a mono- or a di-saccharide.

27. The method of claim 26 wherein said aqueous solution is essentially free of saccharide.

28. The method of claim 9 wherein said aqueous solution contains less than 4 mM calcium chloride.

29. The method of claim 28 wherein said aqueous solution contains is essentially free of calcium chloride.

30. The method of claim 9 wherein said aqueous solution contains less than 150 mM sodium chloride.

31. The method of claim 30 wherein said aqueous solution contains less than 75 mnM potassium chloride.

32. The method of claim 9 wherein said aqueous solution contains less than 15 mM potassiun chloride.

33. The method of claim 32 wherein said aqueous solution contains less than 6 mM potassium chloride.

34. The method of claim 1 wherein said aqueous solution contains less than 100 mOsmol/kg equivalents of a mono- or di-saccharide.

35. The method of claim 34 wherein said aqueous solution is essentially free of saccharide.

36. A method of cleaning a contact lens comprising contacting said contact lens with aqueous solution comprising 0.001 to 10.0 percent by weight of a cationic cellulosic-polymer, a surfactant, provided that the solution has a chloride ion concentration of no more than 300 mM and does not contain an anionic therapeutic agent for the treatment of dry eye.

* * * * *